(12) United States Patent
Nimberger et al.

(10) Patent No.: US 6,539,312 B1
(45) Date of Patent: Mar. 25, 2003

(54) SAMPLING SYSTEM FOR OBTAINING PIPELINE GAS SAMPLES

(75) Inventors: Spencer M. Nimberger, Houston, TX (US); Kevin J. Cessac, Houston, TX (US)

(73) Assignee: PGI International, Inc., Houston, TX (US)

(*) Notice: Subject to any disclaimer, the term of this patent is extended or adjusted under 35 U.S.C. 154(b) by 0 days.

(21) Appl. No.: 09/951,587

(22) Filed: Sep. 13, 2001

Related U.S. Application Data
(60) Provisional application No. 60/233,352, filed on Sep. 18, 2000.

(51) Int. Cl.[7] .................................................. G01N 1/14
(52) U.S. Cl. ............................ 702/24; 702/50; 702/55; 73/863.11; 73/863.84
(58) Field of Search ............................ 702/24, 50, 55; 73/863.61, 861.04, 863.84, 866.5, 40.7, 623, 863.11; 324/220

(56) References Cited

U.S. PATENT DOCUMENTS

| | | | |
|---|---|---|---|
| 5,092,742 A | * | 3/1992 | Allen et al. .................. 417/313 |
| 5,109,709 A | * | 5/1992 | Nimberger ................ 73/863.84 |
| 5,191,801 A | * | 3/1993 | Allen et al. ............... 73/864.34 |
| 6,289,752 B1 | * | 9/2001 | Nimberger et al. ...... 73/863.11 |

* cited by examiner

Primary Examiner—John Barlow
Assistant Examiner—Hien Vo
(74) Attorney, Agent, or Firm—Loren Helmreich; Browning Bushman, P.C.

(57) ABSTRACT

A sample probe 18 for a gas sampling system obtains a highly accurate hydrocarbon gas sample from a pipeline, particularly when ambient conditions are below the hydrocarbon dew point. A compartment 20 houses a heater 44 and a pump 30, with the pump being mounted on an upper body 50 of probe 18 by suitable nuts 56, 58. A lower probe section 48 having coarse threads 76 is mounted within pipeline 10 and has a diameter D1 of at least greater than 80% of the diameter D of internally threaded opening 14 of pipeline 10. Probe 18 has large diameter upper body 50 externally threaded for mounting compartment 20 thereon. Probe 18 is preferably formed of an anodized aluminum material having a high thermal conductivity in excess of 80 BTU/Ft Hr/Ft$^2$/°F.

20 Claims, 2 Drawing Sheets

SAMPLING SYSTEM FOR OBTAINING PIPELINE GAS SAMPLES

REFERENCE TO RELATED APPLICATION

This application claims the benefit of application Ser. No. 60/233,352 filed Sep. 18, 2000.

FIELD OF THE INVENTION

The present invention relates to sample probes of the type which may be used in a gas sampling system. More particularly, the present invention relates to an improved heated gas sampling probe for obtaining a highly accurate sample of gas hydrocarbons passing through a pipeline.

BACKGROUND OF THE INVENTION

A gas sampling system for gas pipelines normally includes a probe, a sample pump and a sample collection bottle. The pump transmits the gas to be sampled through the probe and to the bottle. Sample probes for obtaining gas samples from pipelines normally include a body with a shut off valve along a throughbore, with the lower body threads connected to the pipeline. Extending downward from the body is a lower tubing section, which typically was welded to the body to provide the length necessary for the end of the sample probe to reach the inner third of the cross-section of the pipeline in which it is mounted.

In order to obtain a proper gas sample from the pipeline to the bottle, the sampling equipment between the pipeline and the collection bottle is required to be at a temperature above the dew point of the hydrocarbon gas. When ambient conditions are below the hydrocarbon dew point, it is necessary to apply heat from a heating source to the sampling equipment, including particularly the pump, which then conventionally heats the probe by conduction. The probe may alternatively be heated directly by the heating source. Heating of the sampling equipment may be accomplished by heat trace lines, either electrical or water, or by heating with a catalytic heater that uses pipeline gas for firing the heater to heat the pump and probe by radiant heating. These prior art heating devices have not, however, been capable of selectively heating the full length of the throughbore in the probe, including particularly the full length of the lower probe within the pipeline. Accordingly, the sampled gas temperature drops below its dew point, and the collection bottle does not accurately reflect the BTU content of gas in the pipeline.

Due to the problems with obtaining accurate gas samples in a sample bottle from a hydrocarbon pipeline, it is known to enclose the heater for heating the pump and the associative flow lines from the gas pipeline to the sample bottle. In some cases, the pump and heating system have been enclosed within a relatively large enclosure or "dog house" which includes a portion of the length of the pipeline. The cost of these enclosures is significant, however, and it is generally difficult to provide proper service to the components within the enclosure without removing the entire enclosure from the pipeline.

It is desirable that a sampling system be provided that easily accomplishes heating of the sampling equipment, including particularly the full length of the throughbore in the probe, to a temperature above the dew point of the hydrocarbon gas being sampled.

The disadvantages of the prior art are overcome by the present invention, and an improved sampling system is hereafter disclosed which includes a probe designed to maintain the hydrocarbon gas passing through the probe above it dew point.

SUMMARY OF THE INVENTION

The present invention is directed to a gas sampling system and associated equipment which utilizes a probe supporting the pump and a heater for heating the pump and the probe to a temperature above the dew point of the hydrocarbon gas being sampled. The heater typically heats a pump which then heats the probe by conduction, since both the pump and the probe have metallic bodies. The gas sampling equipment is preferably housed within an enclosure or compartment which contains the pump, the probe, and the sample bottle. A catalytic heater may be used as the heater, and housed in the compartment and fired by gas from the pipeline. Due to improvements in the probe, the heater is particularly effective in thoroughly heating the full length of the throughbore in the probe, including its lower body within the pipeline.

The probe of the present invention comprises a body which preferably supports the enclosure thereon. The probe may be mounted on a pipeline by threading within an internally threaded opening in a weld flange on the pipeline. A lower body of the probe extends within the pipeline a distance ⅓ the inner diameter of the pipeline. The outer diameter of the lower body of the probe is at least about 80% of the inner diameter opening in the weld flange of the pipeline through which it passes when mounted on the pipeline. Fins for increasing the thermal conductivity to the gas passing through the probe are formed by threads on the external surface of the lower body. Thus, the lower body has a relatively large external surface area for high thermal conductivity from the gas in the pipeline to the sampled gas in the throughbore in the lower body.

An intermediate body of the probe may be externally threaded for mounting within the internally threaded opening of the weld flange for the pipeline. An upper body of the probe extends outwardly from the pipeline and preferably has an outer diameter at least 50% greater, and preferably about twice, the inner diameter of the internally threaded opening in the pipeline. A substantial length portion of the upper probe section outwardly of the pipeline is externally threaded to provide a relatively long threaded portion for connection to the enclosure which houses the pump and the probe. The probe is preferably fabricated from a high thermal conductivity metal, and may be made of anodized aluminum having a conductivity in excess of 80 BTU/Ft Hr/Ft$^2$/° F. The relatively large cross-section of the upper probe body provides a large thermal flow path from the heating source to the lower probe body at a rate that overcomes other thermal influences.

An object of the invention is the provision of an elongate probe and heater for effectively heating the probe along its entire length for use in a gas sampling system for sampling hydrocarbon gas in a pipeline.

It is a feature of the invention that the probe may support an enclosure for the sampling equipment mounted on and carried by the probe.

It is a feature of the invention that the probe is fabricated in high thermal conductivity metal, such as anodized aluminum.

A further feature is that the probe has a relatively large diameter upper probe body extending outwardly from the pipeline to provide a large thermal cross-sectional flow path from the heating source to the lower probe body within the pipeline.

A further feature of the invention is that the outer diameter of the lower body of the probe within the pipeline is greater than at least about 80% of the inner diameter of the opening in the pipeline, thereby providing a high cross-sectional flow area for conduction of heat from an upper body of the probe to a lower body within the pipeline.

These and further objects, features and advantages of the invention will be apparent from the following description, wherein reference is made to the Figures in the accompanying drawings.

DESCRIPTION OF THE PREFERRED EMBODIMENTS

Figure 1:
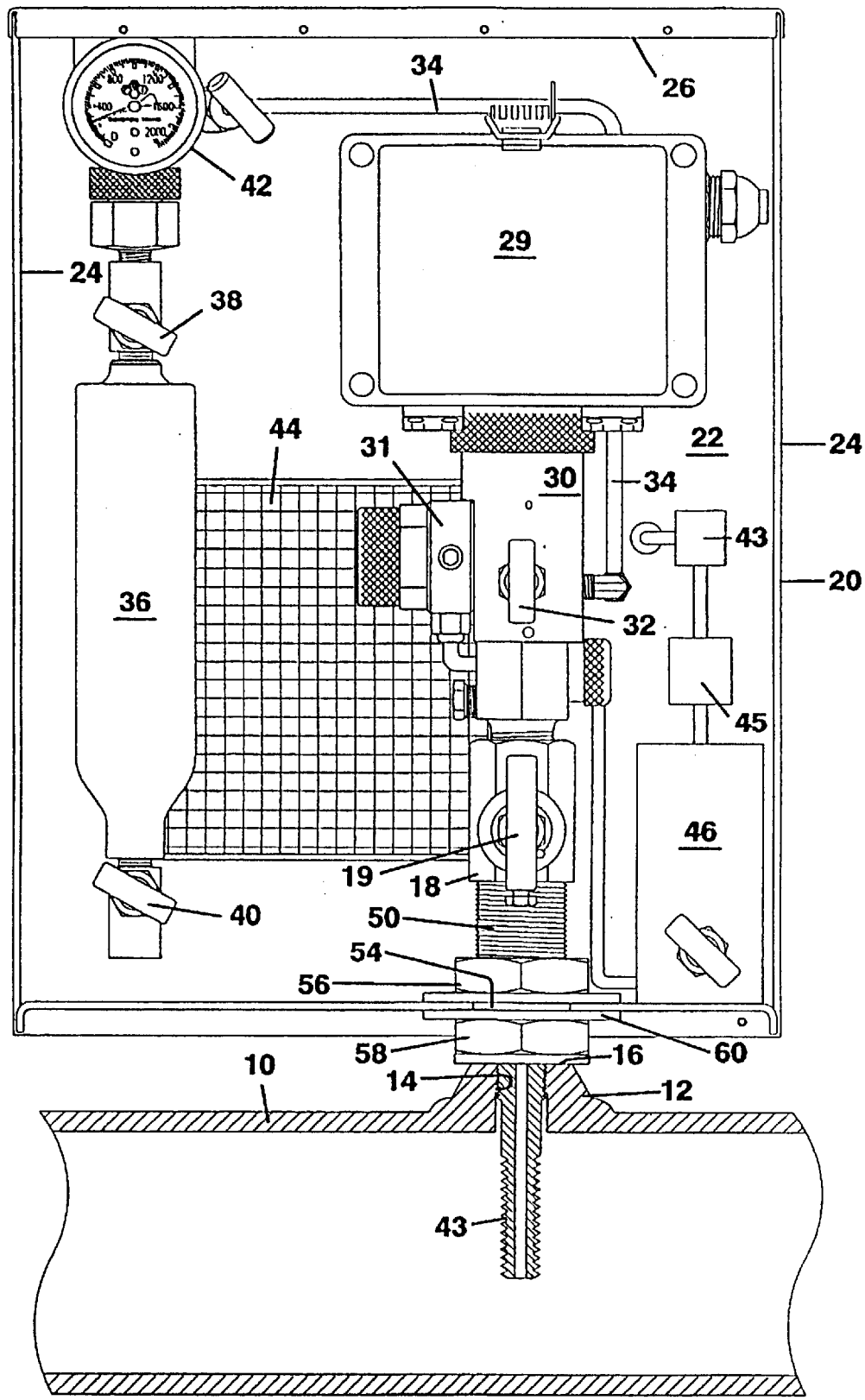
FIG. 1 is a side pictorial view, partly schematic, showing a gas sampling system according to the present invention.

Referring now to FIG. 1, a gas sampling system is shown for obtaining a suitable gas sample from a hydrocarbon gas pipeline 10 having a weld flange 12 defining an internally threaded opening 14 and an outer flat annular surface 16. A probe shown generally at 18 has a shutoff valve 19 and is mounted within internally threaded opening 14. The gas sampling equipment is positioned within a generally rectangular enclosure or compartment 20 that may be entirely supported on probe 18.

Enclosure or compartment 20 has its front panel or face removed to disclose a back panel 22, side panels 24, upper panel 26, and a base panel 28. A sampling pump 30 controls the flow of gas from pipeline 10 through probe 18 and to sample bottle 36. Regulator 31 limits or controls pipeline pressure to an acceptable level to operate pump 30. The sampling pump is operated by an electronic controller 29 for obtaining a sample "bite" of gas at selected time intervals. A valve 32 controls the gas flow from pump 30 through line 34 to a gas sample bottle 36, which has an inlet valve 38 and an outlet valve 40. Pressure gauge 42 is provided along line 34. Bottle 36 may thus be periodically removed and taken to a lab, where one of valves 38 and 40 may be opened to test the sampled gas for its BTU content. A catalytic heater 44 is provided for heating the pump 30 and other sampling equipment, including probe 18. The pump is typically heated, which then heats the probe and the flow lines to the bottle 36 by conduction. Heater 44 may utilize gas from pipeline 10 which passes from regulator 31 through scrubber 46, and then through another pressure regulator 45 and then through thermostat 48, which controls gas flow for firing the catalytic heater 44. Cleaned hydrocarbon gas at a desired pressure is then input to heater 44. Sample bottle 36 is also appropriately positioned within the enclosure, which helps to retain heat from the heater 44 about the various sampling system components within the enclosure. As previously noted, various other types of heaters may be used, including electric or hot fluid trace lines.

Figure 2:
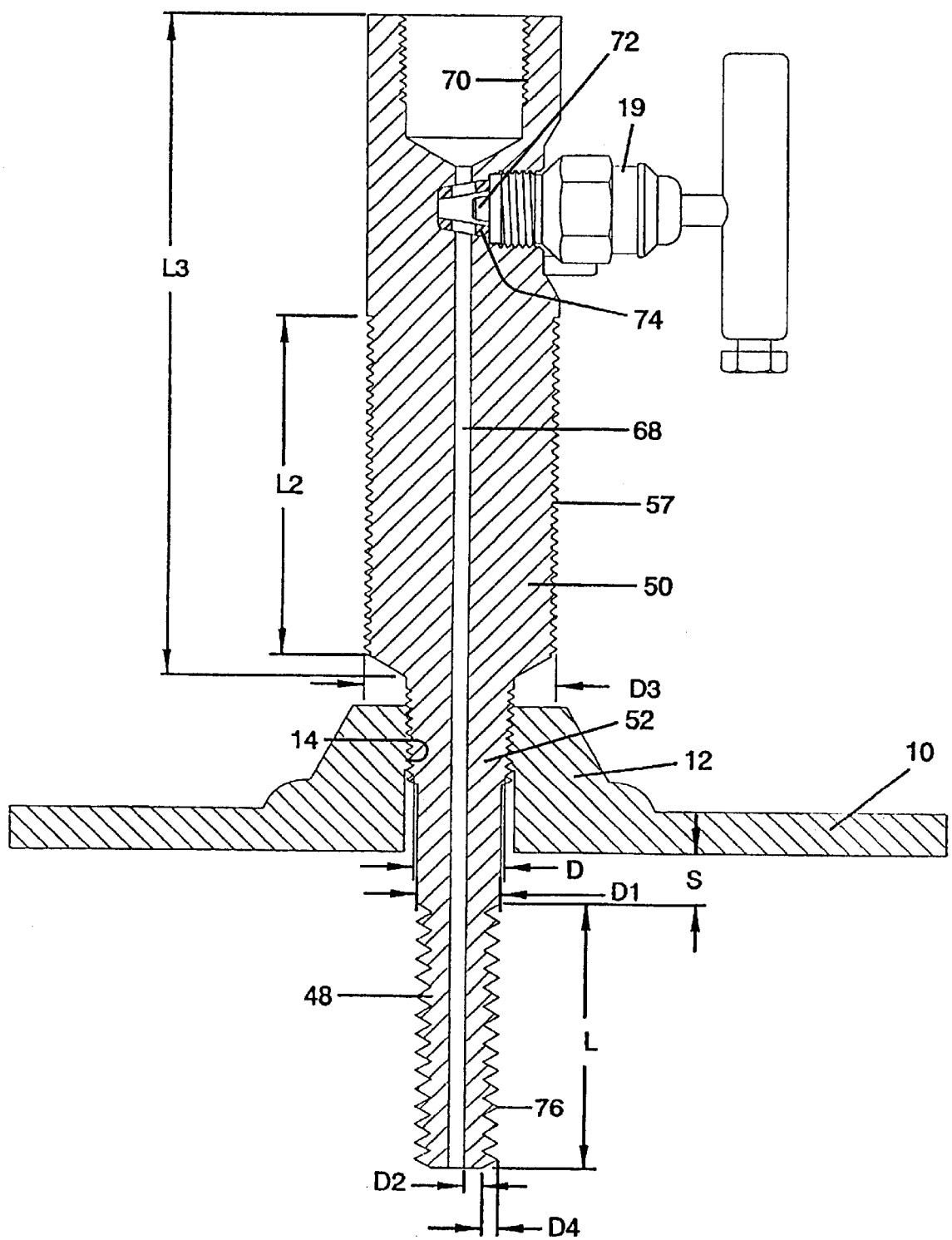
FIG. 2 is an enlarged sectional view of the probe of the present invention used in the system shown in FIG. 1.

Probe 18 as shown in FIG. 2 has a lower body 48 for extending within pipeline 10, an upper body 50 for extending outwardly from pipeline 10, and an externally threaded intermediate body 52 threaded within internally threaded opening 14 of pipeline 10. Upper body 50 has an externally threaded portion 51. Enclosure 20 may be entirely supported on upper probe body 50. As shown FIG. 1, base 28 has an opening 54 receiving upper body 50 and is secured between nuts 56 and 58. Suitable washers 60 are provided for nuts 56 and 58. For mounting of enclosure 20, the probe 18 with the nuts 56 and 58 and the washers 60 thereon is mounted on the pipeline 10. Nut 58 may be threaded to the upper probe body 50 so that the lower washer 60 is in engagement with the outer surface 16 of weld flange 12. Then, compartment 20 may be mounted on upper section 50 by sliding the opening 54 in the enclosure 20 to a desired position. Next, upper washer 60 positioned on probe upper body 50 and nut 56 may be threaded to engage the base 28, thereby supporting enclosure 20 entirely on probe 18, as shown in FIG. 1. While enclosure 20 is shown abutting annular surface 16 on pipeline 10, it may be desirable under some conditions to space compartment 20 outwardly from the pipeline by spacing nuts 56 and 58 outwardly of surface 16, thereby to position compartment 20 at a selected position along the length of threaded upper section 50.

Referring to FIG. 2, the threaded portion 51 of upper body 50 has a length L2 which is at least about one-half of the length L3 of upper section 50 to permit the adjustment of enclosure 20 along threaded portion 51. The length L2 of the threaded portion 51 is preferably over about 2 inches. This relatively long threaded length L2 on the upper body also permits the upper and lower nuts to be spaced substantially apart so that a flange or other member affixed to the enclosure 20 may pass between the spaced apart nuts when the enclosure is removed from the probe. Lower nut 58 may act as a stabilizer for probe 18 when nut 58 is tightly mounted against weld flange 12. It may be desirable when spacing enclosure 20 from pipeline 10 to maintain nut 58 against weld flange 12 for stabilizing probe 18 and then provide an additional nut for mounting enclosure 20 between upper and lower nuts.

Upper body 50 has an outer diameter D3 at threaded portion 51 substantially larger than diameter D of opening 14 in pipeline 10 to provide a relatively large cross-sectional area (in the horizontal plane, as shown in FIG. 2) for said thermal conductivity from upper body 50 to lower body 48. The portion of body 50 above the threaded portion 51 may have a hex configuration, as shown in FIG. 1, with a cross-section greater than that of the threaded portion. For a ½ inch NPT thread 14, diameter D3 of the threaded portion is at least 50% greater and preferably 75% greater than diameter D for best results. For a ¾ inch NPT thread 14, diameter D3 of the threaded portion is greater than the diameter D, and preferably at least 25% greater than diameter D.

As shown in FIG. 2, the probe according to the present invention preferably is a unitary one-piece construction, with the entire probe body preferably being formed from aluminum with a high thermal conductivity. A high thermal conductivity for the upper body 50 is required so that heat from the pump may be transmitted downward through the upper body to heat the intermediate body 52 and the lower body 48. Lower body 48 preferably has external fins so that heat from the hydrocarbon gas in the pipeline can be used to assist in heating the sample gas in the throughbore in the lower body 48 and in the intermediate body 52.

In a less desirable alternative, the body of the probe could be made from two or more pieces. In one alternative, an outer threaded collar formed from a less thermally conductive material, such as stainless steel could be threaded to the pipeline, then the probe threaded or otherwise affixed within the annular collar. The theoretical advantage of this embodiment is that a low thermal conductivity material is present between the pipeline and the probe. A significant disadvantage of this embodiment, however, is that the cross-sectional area of the probe in the vicinity of the intermediate body 52 is inherently reduced. The reduced cross-sectional area practically limits the amount of heat that can be transmitted from the upper body 52 to lower body 48, and accordingly a one-piece and substantially homogeneous metal body is preferred.

As indicated above, gas within the sampling pump 30 and probe 18 has to be maintained at a temperature above the hydrocarbon dew point of the gas being sampled in order to obtain a proper gas sample. Probe 18 is particularly designed for efficiently heating the entire length of the throughbore through the probe. When ambient conditions are such that a heater is required for heating the sampling equipment, it is important that probe 18 be thoroughly heated for proper operation of the sampling system in obtaining an accurate sample.

Probe 18 is preferably a one-piece structure formed of aluminum having a high thermal conductivity in excess of 80 BTU/Ft Hr/Ft$^2$/° F., and typically from 80 and 200 BTU/Ft Hr/Ft$^2$/° F. The aluminum body may be hard anodized to limit corrosion and increase abrasive resistance. A central throughbore 68 extends the entire length of probe 18 and has an enlarged internally threaded upper bore portion 70 to receive pump 30 therein. Shutoff valve 19 has an end plug 72 to close off against seal 74 upon manual operation. Lower probe body 48 extends within pipeline 10 to about ⅓ the internal diameter of pipeline 10 for taking the gas sample. External diameter D1 of lower probe body 48 is preferably formed of a maximum diameter for easily passing through inner diameter D of the internally threaded opening 14 in pipeline 10, and is at least 80% of diameter D. Diameter D1 is preferably above 90% of diameter D for best results. External threads 76 on the outer surface of lower probe section 48 define fins to provide a relatively large outer surface area for heat to be conducted to probe 18 from the gas in pipeline 10, since the gas in the pipeline is typically warmer than the metal material of pipeline 10 when the probe and pump are heated. Threads 76 are spaced a distance S from the inner peripheral surface of pipeline 10 at least about ½ inch and preferably between ½ and 1 inch from the inner periphery of pipeline 10. To provide a relatively large surface area, coarse threads 76 are provided which have a thickness or depth shown at D4 which may be generally the same as the wall thickness D2 of lower section 48 without the threads. A preferred depth or thickness of threads 76 is preferably from 60% to 140% of the wall thickness D2 of lower body 48. The length L of the externally threaded portion of inner section 48 is a function primarily of the diameter of the pipeline.

The terms "upper" and "lower" when used with respect to the body of the probe are not intended to require that the probe be mounted on the top of the pipeline, although that is its preferred positioning when the probe supports the pump and enclosure. The "upper" body is that body portion which extends radially outward from the pipeline, while the "lower" body is that portion which will extend radially into the pipeline when the body is mounted on the pipeline.

From the above, it is apparent that a gas sampling system has been provided for obtaining an accurate gas sample from a hydrocarbon gas pipeline, particularly when ambient conditions are below the hydrocarbon dew point. Probe 18 is specially constructed for supporting a sampling equipment enclosure thereon and for being thoroughly heated to provide a large thermal flow path from the large diameter upper section to the relatively small diameter lower section within the pipeline. The probe may be used, however, without an enclosure. Insulation may be used to reduce heat losses from the pump, probe, or flow lines, particularly if an enclosure is not utilized. Also, the pump may not be supported on the probe, and tubing may connect the probe to a pump supported on the pipeline separate from the probe.

While a preferred embodiment of the present invention has been illustrated in detail, it is apparent that modifications and adaptations of the preferred embodiment will occur to those skilled in the art. However, it is to be expressly understood that such modifications and adaptations are within the spirit and scope of the present invention as set forth in the following claims.

What is claimed is:

1. A sampling probe for mounting within an opening in a hydrocarbon gas pipeline for obtaining sample gas from the pipeline, the probe supplying gas to a pump for sampling gas from the pipeline through the probe and to a sample bottle while the pump and probe are heated by a heater to minimize condensation of gas between the pipeline and the sample bottle, said probe comprising:
    a lower body with a throughbore for extending within the pipeline;
    an upper body with a connected throughbore for extending outwardly from said pipeline;
    said upper body and said lower body being rigidly connected and formed from a metal having a thermal conductivity of at least 80 BTU/Ft Hr/Ft$^2$/° F.; and
    an outer diameter of said lower body of said probe being greater than at least about 80% of an inner diameter of said opening in said pipeline.

2. The sampling probe as defined in claim 1, wherein an outer surface of said lower body has outwardly extending fins along a majority of a length of said lower body within an interior surface of the pipeline.

3. The sampling probe as defined in claim 2, wherein said outwardly extending fins comprise screw threads on the outer surface of said lower body.

4. The sampling probe as defined in claim 3, wherein said screw threads have a depth between 60% and 140% of a wall thickness of said lower body containing said screw threads.

5. The sampling probe as defined in claim 1, wherein said probe has an intermediate body between said lower body and said upper body, the intermediate body being externally threaded for engaging internal threads defining said opening in said pipeline.

6. The sampling probe as defined in claim 5, wherein said upper body, intermediate body, and said lower body are a unitary metal piece.

7. The sampling probe as defined in claim 1, wherein said upper body has a threaded portion, and an outer diameter of said threaded portion is at least 25% greater than an inner diameter of said opening in said pipeline.

8. The sampling probe as defined in claim 1, wherein the upper body includes threads supporting the pump on the probe.

9. A sampling system for obtaining sample gas from a hydrocarbon gas pipeline, comprising:
    a pump for pumping gas from the pipeline to a sample bottle;
    a controller for controlling operation of the pump;
    a heater for heating the pump to minimize condensation of gas between the pipeline and the sample bottle;
    a generally enclosed container for housing the pump, the heater, and at least a portion of a probe therein; and
    the probe for mounting in an opening in the pipeline and extending upwardly into said container, said probe including a lower body with a throughbore for extending within the pipeline and an upper body with a connected throughbore for extending outwardly from said pipeline, said upper body including a threaded portion having external threads thereon, said generally enclosed container being mounted on said threaded portion of said upper body for supporting said container.

10. The sampling system as defined in claim 9, wherein said container has a lower base with an opening therein for receiving said upper body; and a pair of nuts on opposed sides of said lower base for engagement with said threaded portion of said lower section for mounting said container thereon.

11. The sampling system as defined in claim 9, wherein an outer diameter of said lower body of said probe is greater than at least about 80% of an inner diameter of said opening in said pipeline.

12. The sampling system as defined in claim 9, wherein said probe has an intermediate body between said lower body and said upper body, said intermediate body being externally threaded for engaging internal screw threads defining said opening in said pipeline.

13. The sampling system as defined in claim 12, said upper body, said intermediate body, and said lower body are a unitary and substantially homogeneous metal piece.

14. The sampling system as defined in claim 9, wherein said probe is formed of anodized aluminum having a high thermal conductivity of at least 80 BTU/Ft Hr/Ft$^2$/° F.

15. The sampling system as defined in claim 9, wherein an outer surface of said lower body has outwardly extending fins along a majority of a length of said lower body within an interior surface of the pipeline.

16. A sampling probe for mounting within an opening in a hydrocarbon gas pipeline for obtaining sample gas from the pipeline, the probe supporting a pump for sampling gas from the pipeline through the probe and a sample bottle while the pump and probe are heated by a heater to minimize condensation of gas between the pipeline and the probe, said probe comprising:

a lower body with a throughbore for extending within the pipeline;

an upper body with a connected throughbore for extending outwardly from said pipeline;

said upper body and said lower body each being formed from a metal having a thermal conductivity of at least 80 BTU/Ft Hr/Ft$^2$/° F.; and and outer surface of said lower body having outwardly extending fins along a majority of the length of said lower body.

17. The sampling probe as defined in claim 16, wherein said probe has an intermediate body between said lower body and said upper body, the intermediate body being externally threaded for engaging internal threads defining said opening in said pipeline, and said upper body, intermediate body, and said lower body are a unitary metal piece.

18. The sampling probe as defined in claim 16, wherein an outer diameter of said fins is at least about 80% of an inner diameter of said opening in said pipeline.

19. The sampling probe as defined in claim 16, wherein said upper body has a cross-sectional area at least about 25% greater than an inner diameter of said opening in said pipeline to form a large area thermal flow path from said upper body to said lower body.

20. The sampling probe as defined in claim 16, wherein said fins comprise screw threads having a depth between 60% to 140% of a wall thickness of said lower body containing said threads.

* * * * *